United States Patent
Shalaby et al.

(10) Patent No.: US 9,028,860 B2
(45) Date of Patent: May 12, 2015

(54) PARTIALLY MICROCELLULAR, SELECTIVELY HYDROPHILIC COMPOSITE CONSTRUCT FOR OCULAR DRUG DELIVERY

(75) Inventors: Shalaby W. Shalaby, Anderson, SC (US); Joel T. Corbett, Anderson, SC (US); Jason M. Olbrich, Clemson, SC (US)

(73) Assignee: Poly-Med, Inc., Anderson, SC (US)

( * ) Notice: Subject to any disclaimer, the term of this patent is extended or adjusted under 35 U.S.C. 154(b) by 205 days.

(21) Appl. No.: 13/096,377

(22) Filed: Apr. 28, 2011

(65) Prior Publication Data
US 2011/0268783 A1 Nov. 3, 2011

Related U.S. Application Data

(60) Provisional application No. 61/343,388, filed on Apr. 28, 2010.

(51) Int. Cl.
| | |
|---|---|
| *A61F 2/14* | (2006.01) |
| *A61K 9/00* | (2006.01) |
| *A61K 9/19* | (2006.01) |
| *A61K 31/085* | (2006.01) |
| *A61K 31/4164* | (2006.01) |
| *A61K 31/573* | (2006.01) |

(52) U.S. Cl.
CPC ............. *A61K 9/0051* (2013.01); *A61K 9/0009* (2013.01); *A61K 9/19* (2013.01); *A61K 31/085* (2013.01); *A61K 31/4164* (2013.01); *A61K 31/573* (2013.01)

(58) Field of Classification Search
USPC ........................................................ 424/427
See application file for complete search history.

(56) References Cited

U.S. PATENT DOCUMENTS

| | | | | |
|---|---|---|---|---|
| 4,186,184 | A * | 1/1980 | Zaffaroni | 424/427 |
| 5,147,647 | A * | 9/1992 | Darougar | 424/427 |
| 6,264,971 | B1 * | 7/2001 | Darougar et al. | 424/427 |

* cited by examiner

*Primary Examiner* — Michael B Pallay
(74) *Attorney, Agent, or Firm* — McNair Law Firm, P.A.; Douglas L. Lineberry

(57) ABSTRACT

A partially microcellular, selectively hydrophilic composite as a self-standing construct or a component of a device for ocular delivery of at least one bioactive agent, the composite comprising a highly hydrophilic microcellular foam adjoined with a flexible hydrophobic barrier polymeric film.

20 Claims, 3 Drawing Sheets

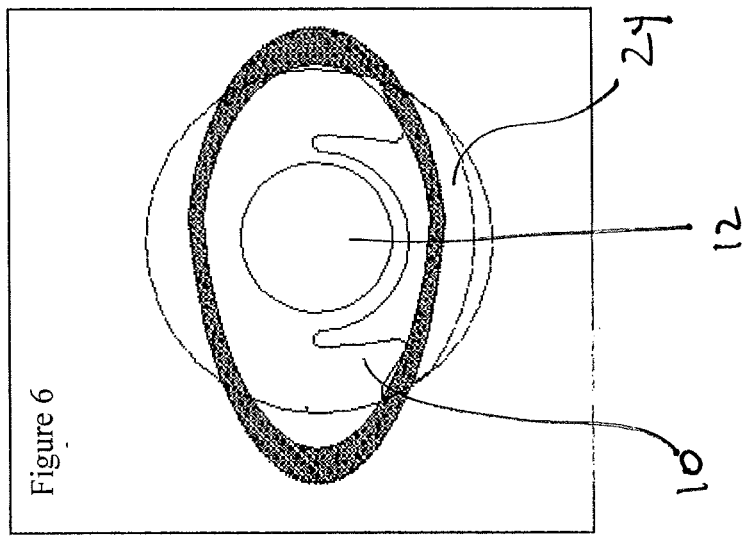
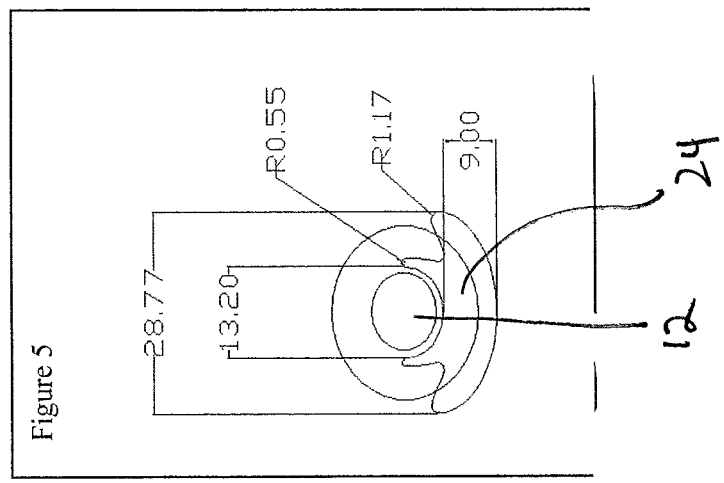
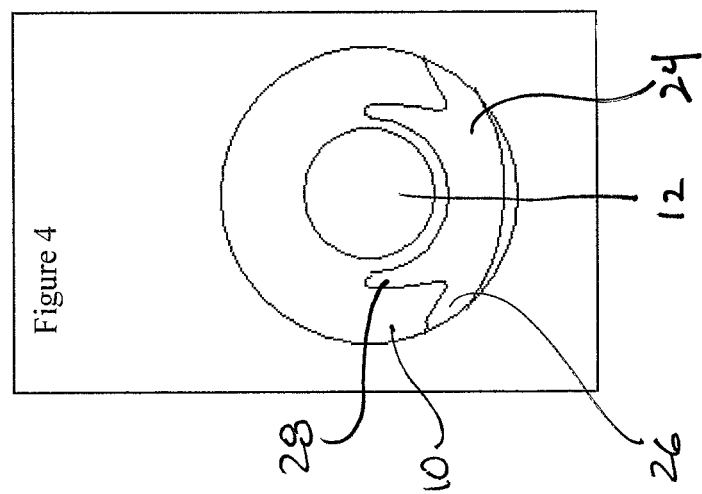

PARTIALLY MICROCELLULAR, SELECTIVELY HYDROPHILIC COMPOSITE CONSTRUCT FOR OCULAR DRUG DELIVERY

CROSS REFERENCE TO RELATED APPLICATION

This application claims the benefit of U.S. Provisional Patent Application Ser. No. 61/343,388 filed on Apr. 28, 2010, which is herein incorporated by reference in its entirety.

FIELD OF THE INVENTION

This invention is directed generally to a composite construct for ocular drug delivery and non-particularly to a partially microcellular, selectively hyodrophyllic composite construct for the active delivery of bioactive agents.

BACKGROUND OF THE INVENTION

In a report by Kim and Chauhan [*Internat. J. Pharm*, 353, 204 (2008)], the authors noted that (1) most treatments of ocular diseases are still based on topical applications of eye drops to the surface of the eye in spite of the many novel approaches which have been developed over the past two decades; (2) after application of an eye drop, the drug solution mixes with tear fluid and then within five minutes, the majority of the drug (95-99%) is eliminated by tear drainage and conjunctival uptake—in order to maintain therapeutic levels of drug concentration, frequent instillation of drops with large drug loadings are required which is inconvenient to the patient with possible side effects; (3) to overcome the drawbacks of the drops, several ophthalmic drug delivery systems have been proposed, such as suspension of nanoparticles, liposomes, ocular inserts (e.g., collagen shields and Ocusert®) and therapeutic contact lenses; and (4) on instillation of medicated contact lens in the eye, the drug diffuses through the lens matrix into the thin tear film named post-lens tear film (POLTF) trapped between the lens and cornea, thus permitting the drug to have a residence time of about 30 minutes in the eye, which increases the drug bioavailability by about an order of magnitude longer than the drops.

In an earlier review by LaBaurlais and coworkers [*Progress in Retinal and Eye Research*, 17, 33 (1998)] intended to accelerate the transport of methylprednisolone to the eye tissues, the authors used transscleral column-controlled iontophoresis with the platinum electrode in contact with the drug solution in the cup-shaped reservoir in a silicone applicator, placed on the intact rabbit conjunctiva and sclera adjacent to the limbus while placing the positive electrode on the rabbit ear.

In concert with the above-noted technical literature in ocular drug delivery, U.S. Patent Application, Serial No. 2004/0071761 singled out the topical application of drug as a facile route of administration in spite of certain drawbacks associated primarily with drug loss through tear drainage and conjunctival uptake. This application also claimed a pharmaceutical formulation for the treatment of posterior ocular conditions comprising an effective amount of a therapeutic compound and at least one means of enhancing the transport of the therapeutic compound across the sclera of an eye toward and into at least one of an intermediate and posterior portions of the eye and means for prolonging the residence time of the therapeutic compound within the intermediate and posterior portions of the eye. Towards achieving this, the inventor described the preferred use of a gauze pad having the pharmaceutical compound impregnated therein. Alternatively, the inventor described the use of a patch, a sponge, a hydrogel, a porous ceramic or silicone-based membrane as substitutes for the gauze.

Analysis of the aforementioned discussion of the different approaches to ocular drug delivery indicate that (1) topical drug application is the most non-invasive mode of administration; (2) traditional use of eye drops is least effective for a timely delivery of therapeutic drugs; (3) a drug carrier of well-defined geometry that adheres to the sclera and localizes the drug availability to the specific interface between the carrier and the sclera; (4) the lack of an easy-to-deploy, patient-friendly topical drug delivery system; (5) rapid release of the therapeutic agent in high concentrations is most effective; and (6) iontophoresis can be used to accelerate the release rate of the drug from a properly designed drug release system for topical application. This prompted exploring the study subject of this invention, which deals primarily with a composite construct comprising an hydrophilic microcellular foam as a drug carrier adjoined with flexible hydrophobic barrier film to facilitate handling and directing the drug transport. The release rate of the drug can be accelerated through incorporating the construct in an iontophoretic transscleral delivery system.

SUMMARY OF THE INVENTION

An embodiment of the invention generally deals with a partially microcellular, selectively hydrophilic composite as a self-standing construct or a component of a device for ocular delivery of at least one bioactive agent, the composite comprises a highly hydrophilic microcellular foam adjoined with a flexible hydrophobic barrier polymeric film, wherein the highly hydrophilic microcellular foam comprises an open cell structure of at least one freeze-dried polymer selected from the group consisting of polyvinyl alcohol or poly(vinyl alcohol-co-vinyl acetate), an hydroxyalkyl cellulose, polyethylene oxide, polyvinyl pyrrolidone, poly(vinyl acetate-co-vinyl pyrrolidone), a polyether-ester, a polyether-ester-urethane, poly(methyl methacrylate-co-vinyl pyrrolidone), poly(ethylene-co-vinyl alcohol), and poly(hydroxy-ethyl methacrylate-co-alkyl methacrylate), and wherein the flexible hydrophobic barrier polymeric film comprises at least one polymer selected from the group consisting of polydimethylsiloxane, poly-ε-caprolactone, polyethylene adipate, polytetramethylene adipate, low density polyethylene, poly(ethylene-vinyl acetate), and a polyalkylene succinate and further wherein the flexible hydrophobic barrier film is made by compression molding or solution casting and adjoined with the microcellular foam by thermoforming at 50 to 150° C., solvent or ultrasonic welding, or crosslinkable prepolymeric intermediates. The said flexible hydrophobic barrier film itself exhibiting a flexural modulus of less than 30 MPa, a tensile strength of more than 50 Kpsi, an ultimate elongation of at least 200%, and melts or softens below 150° C. while the assembled composite construct, presoaked for less than 10 minutes with water using about 100 μL per 120 mm³, displaying a flexural modulus of less than 1 MPa.

Another embodiment of the invention deals with a partially microcellular, selectively hydrophilic composite as a self-standing construct or a component of a device for ocular delivery of at least one bioactive agent, the composite comprises a highly hydrophilic microcellular foam adjoined with a flexible hydrophobic barrier polymeric film, wherein the highly hydrophilic microcellular foam comprises an open cell structure of at least one freeze-dried polymer selected from the group consisting of polyvinyl alcohol or poly(vinyl alcohol-co-vinyl acetate), an hydroxyalkyl cellulose, polyethylene oxide, polyvinyl pyrrolidone, poly(vinyl acetate-co-vinyl pyrrolidone), a polyether-ester, a polyether-ester-urethane, poly(methyl methacrylate-co-vinyl pyrrolidone), poly(ethylene-co-vinyl alcohol), and poly(hydroxy-ethyl methacrylate-co-alkyl methacrylate), and wherein the freeze-dried foam is designed to have a thickness of 1 to 3 mm, a pore fraction of at least 0.5 to 0.9 and an average pore diameter of 1 to 400 microns with said composite comprising soluble or dispersed solid nanoparticles or microparticles of at least one bioactive agent selected from the group consisting of steroidal or non-steroidal anti-inflammatory drugs, vasoconstricting drugs, antimicrobial agents, antiviral agents, antiretroviral agents, antineoplastic agents, and drugs used for treating glaucoma and other eye disorders. More specifically, the steroidal anti-inflammatory drug is dexamethasone disodium phosphate, the vasoconstricting drug is oxymetazoline, and the antimicrobial drug is triclosan or triclosan sodium. Additionally, the freeze-dried foam is suitable for loading with a solution of the drug(s) in less than 15 minutes and preferably less than 10 minutes and more preferably less than 5 minutes and delivering of at least 30% of its drug payload at the ocular site in less than 15 and preferably in less than 10 minutes and most preferably in less than 5 minutes.

Another embodiment of the invention deals with the foam/film composites described above with their hydrophilic microcellular foam loaded with steroidal anti-inflammatory drug, such as dexamethasone disodium phosphate, and a vasoconstricting drug, such as oxymetazoline, and an antimicrobial drug, such as triclosan and triclosan sodium.

Another embodiment of the instant invention deals with the foam/film composites described above loaded with an aqueous solution of at least one bioactive agent selected from the group consisting of steroidal and non-steroidal drugs, vasoconstricting drugs, antimicrobial drugs, antineoplastic drugs, antiviral and antiretroviral agents, and drugs used for treating glaucoma and other eye disorders, wherein the steroidal agent is dexamethasone disodium phosphate, the vasoconstricting drug is oxymetazoline and the antimicrobial drug is triclosan or triclosan sodium.

Another embodiment of the invention deals with a partially microcellular, selectively hydrophilic composite as a self-standing construct or a component of a device for ocular delivery of at least one bioactive agent, the composite comprises a highly hydrophilic microcellular foam adjoined with a flexible hydrophobic barrier polymeric film and said composite in the form of a ring-shaped disc affixed to an applicator wherein said disc is designed to have a lumen diameter which exceeds that of the cornea by at least 10% and preferably by more than 20% and more preferably by more than 30% and a difference between the outside and inside diameter of at least 3 mm, and capable of covering at least 30% of the accessible scleral surface.

Another embodiment of the invention is partially microcellular, selectively hydrophilic composite that is a self-standing construct or a component of a device for ocular delivery of at least one bioactive agent, the composite comprises a highly hydrophilic microcellular foam adjoined with a flexible hydrophobic barrier polymeric film, wherein the said composite is a component of an iontophoretic ocular delivery device of at least one bioactive agent wherein a flexible conductive film or mesh is sandwiched securely between the hydrophilic microcellular foam and the hydrophobic barrier film and the said conductive film or mesh is further connected to one pole of a direct current mini-battery to function as an iontophoretic system with the mammalian ear or adjacent facial tissue being the counter pole of the circuit to allow the iontophoretic transport of the drug from the microcellular foam to the sclera and underlying eye tissues.

Another embodiment of the invention is a partially microcellular, selectively hydrophilic composite that is a self-standing construct or a component of a device for ocular delivery of at least one bioactive agent, the composite comprises a highly hydrophilic microcellular foam adjoined with a flexible hydrophobic barrier polymeric film, wherein said composite is a self-standing construct, crescent-shaped ocular drug delivery device with rounded free ends at a distance exceeding the radius of a typical mammalian eye cornea by at least 10%, and wherein the crescent-shaped device is designed for initial deployment at the rim of the conjunctiva for subsequent upward movement to partially cover the sclera forming a POLTF-like film without interfacing with the cornea through vertical or horizontal movement, and by having two lateral flaps extending toward the sides of a mammalian eye (1-3 mm from the limbus) to further stabilize the position of the device at the application site.

Another embodiment of the invention deals with a partially microcellular, selectively hydrophilic composite as a self-standing construct or a component of a device for ocular delivery of at least one bioactive agent, the composite comprises a highly hydrophilic microcellular foam adjoined with a flexible hydrophobic barrier polymeric film, wherein said composite is in the form of a ring-shaped disc affixed to an applicator wherein said disc is designed to have a lumen diameter which exceeds that of the cornea by at least 10%, and a difference between the outside and inside diameter of at least 3 mm, and capable of covering at least 30% of the accessible scleral surface.

Another embodiment of the invention deals with a partially microcellular, selectively hydrophilic composite as a self-standing construct or a component of a device for ocular delivery of at least one bioactive agent, the composite comprises a highly hydrophilic microcellular foam adjoined with a flexible hydrophobic barrier polymeric film, the said composite is a component of an iontophoretic ocular delivery device of at least one bioactive agent wherein a flexible conductive film or mesh is sandwiched securely between the hydrophilic microcellular foam and the hydrophobic barrier film and the said conductive film or mesh is further connected to one pole of a direct current mini-battery to function as an iontophoretic system with the mammalian ear or adjacent facial tissue being the counter pole of the circuit to allow the iontophoretic transport of the drug from the microcellular foam to the sclera and underlying eye tissues, and wherein the flexible film or mesh of the iontophoretic delivery system is made of a highly conductive metal or surface- or bulk-conducting polymer having a maximum thickness of less than 500 micron, and further wherein the metal film or mesh is comprising at least one metal selected from the group consisting of silver, gold, platinum, titanium, copper and different iron or chrome alloys, the surface conducting polymer comprises a sulfonated polyalkylene and bulk-conducting polymer comprising carbon fibers.

BRIEF DESCRIPTION OF THE DRAWINGS

The present invention will be better understood from reading the following description of non-limiting embodiments, with reference to the attached drawings, wherein below:

FIG. 4 is a schematic front view of an ocular drug delivery system in accordance with an alternative embodiment of the present invention.

FIG. 5 is an additional schematic front view of the ocular drug delivery system of FIG. 4 illustrating location of the device relative to a cornea and sclera.

FIG. 6 is an additional schematic front view of the ocular drug delivery system of FIG. 5.

DETAILED DESCRIPTION OF PREFERRED EMBODIMENTS

Figure 1:
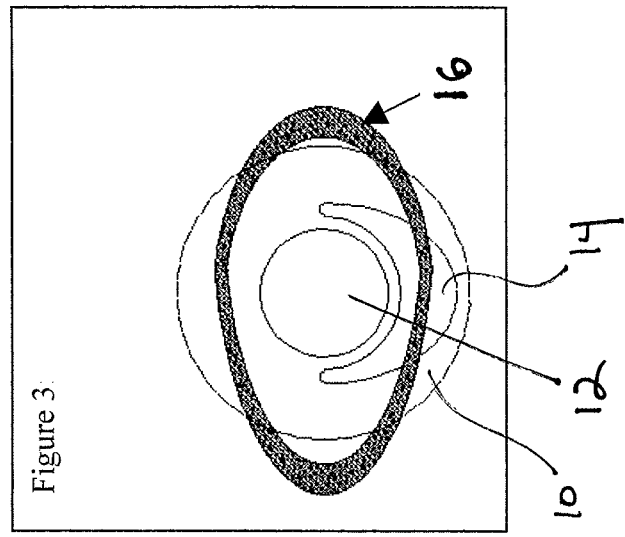
FIG. 1 is a schematic front view of an ocular drug delivery system in accordance with an embodiment of the present invention.

An embodiment of the present invention deals with ocular drug delivery systems that are designed to circumvent known and potential drawbacks associated with those of the prior are for treating practically all eye diseases and disorders through innovative use of established scientific and engineering principles to produce affordable, clinically sound devices and without compromising the patients' comfort, while insuring their compliance. This invention addresses three major aspects of the ocular drug delivery system. The first deals with the design of the device components and the composition thereof. The second aspect addresses the deployment of the device and its positional stability at the intended site. The third aspect deals with the diversity of the pharmaceutical compounds and their release at the application site.

As stated, topical application of eye drops can be associated with over 90% of drug loss. Accordingly, this invention deals with a topical administration from a highly hydrophilic microcellular foam (with an open cell structure) that contains an aqueous solution of the drug (or bioactive agent) at high concentration to allow the transport of the therapeutic dose of said drug in less than 15 minutes and preferably in less than 10 minutes and more preferably in less than 5 minutes. To maximize the contact area between the hydrophilic drug-bearing foam to the sclera and avoid leaking or migration of the drugs, and particularly those which can be harmful to the cornea (1) the delivery device is designed to be reasonably distant of the cornea, but covering a maximum area of the sclera; (2) a tight seal, through a high surface tension of liquid film can be formed between the sclera and the foam by using water as a solvent for the drugs; and (3) fast equilibration between the sclera and the foam through a POLTF-like (post-lens tear film-like). Accordingly, an embodiment of the present invention contemplates the use of highly water-soluble drugs.

Moreover, as previously stated, increasing the residence time to about 30 minutes can increase the drug bioavailability significantly. However, in the instant invention, the strategy for increasing the bioavailability without exceeding significantly 5 minutes and preferably 10 minutes is based on (1) maximizing the contact area of the sclera and the loaded foam; (2) maximizing the percent of the drug in the foam up to 50% without compromising the desirable liquid dynamics between the drug-preloaded foam and the applied aqueous solvent; (3) using hydrophilic foam with variable degrees of hydrophilicity to allow modulating the residence time in concert with the teaching of items 2 and 3; (4) preventing the leakage of the drug solution beyond the scleral contact area by using a self-standing device having a crescent shape that can be placed on the sclera at the edge of the conjunctiva and moved upward without contacting the cornea at any time as in the crescent-shaped device or using a flat, ring-shaped disc that is fixed perpendicularly at the proximal perimeter of a tubular applicator (see FIGS. 1 to 7); (5) restricting the contact area to the sclera through preventing migration of the device laterally by using side flaps extending from the center of the crescent device toward the limbus; (6) adjoining the crescent-shaped device on the surface opposite to the releasing surface, with a hydrophobic barrier film which can selectively direct the drug migration toward the sclera—more specifically, the contacting virtual internal diameter of the crescent-shaped device exceeds the diameter of the cornea more than 10% and preferably more than 20% and more preferably by 40% in order to direct the drug release away from the cornea; and (7) upon using the drug carrier as part of a tubular applicator to facilitate establishing a sclera/drug carrier interface, with a disc-like drug carrier affixed to the contacting edge of the tubular applicator where a cross-sectional area of either the circular or ellipsoidal tube cross-section is larger than that of the cornea by more than 10% and preferably by more than 20% and more preferably by 40%.

Furthermore, as alluded to herein, a preferred ocular device should be least invasive, can be deployed easily to the eye, be biomechanically compatible and conform well to the contour of the contacting eye tissue as in the case of the sclera. Accordingly, the composite crescent or disc comprises (1) a flexible foam in a laminated foam-film composite having a flexural modulus of less than 70 MPa and preferably less than 50 MPa and more preferably more than 30 MPa, which becomes a highly compliant composite with a flexural modulus of less than 20 MPa and preferably less than 1 MPa and more preferably less than 0.5 MPa after conditioning with water, simulating the actual use conditions; and (2) a hydrophobic flexible film having a tensile strength of more than 60 Kpsi and 55 Kpsi under dry and simulated use conditions, respectively, but a tensile modulus under simulated use conditions of less than 250 MPa and preferably less than 200 MPa and more preferably less than 120 MPa.

Figure 2:
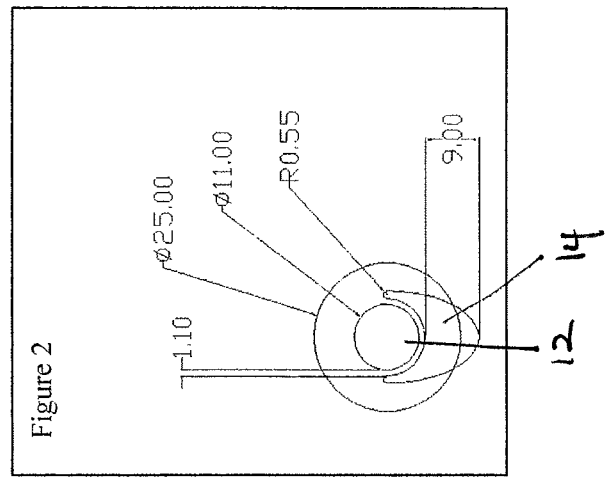
FIG. 2 is an additional schematic front view of the ocular drug delivery system of FIG. 1 illustrating location of the device relative to a cornea and sclera.
Figure 3:
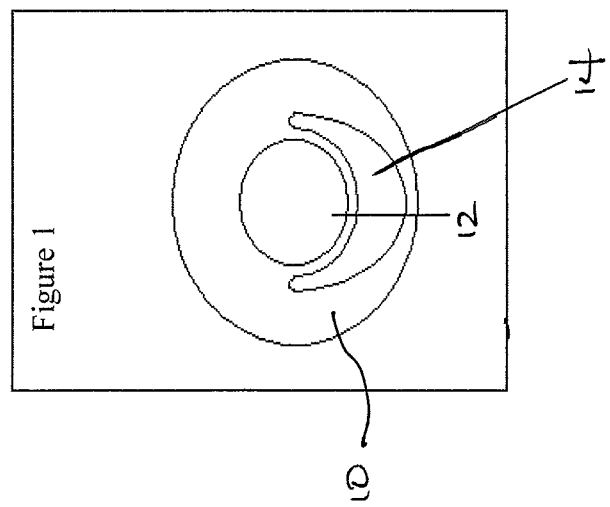
FIG. 3 is an additional schematic front view of the ocular drug delivery system of FIG. 1.

Referring now to FIGS. 1-3, an embodiment of the inventive ocular device 14 is a crescent shaped foam/film composite that is configured to be placed on a sclera 10 of an eye in proximity to, but still reasonably distant from, the cornea 12. As will be appreciated, the foam component of the device 14 is on the side of the device in contact with the sclera 10 so that a drug in the foam may be delivered to the wearer. The crescent shape and dimensions of the device 14 allows the device 14 to closely fit the shape of the sclera 10 and fit comfortably underneath a wearer's eyelid 16.

Turning to FIGS. 4-6, an embodiment of the crescent shaped ocular device 24 may include wings. In particular, the device 24 may include upper and lower wings, 28, 26 respectively, to further facilitate a form fit with a wearer's sclera 10.

In an alternative embodiment, the device may be a foam/film composite ring or disc 26 that is delivered to the sclera through the use of a tubular applicator 28. In this embodiment, the disc 26 is placed around the cornea. As with the above embodiments, the foam component of the disc 26 is on the side of the disc 26 in contact with the sclera 10 so that a drug in the foam may be delivered to the wearer.

Further illustrations of embodiments of the present invention are provided by the following examples:

Example 1

General Method of Preparing Microcellular Foam by Freeze Drying

The specific solution was lyophilized using a Labconco Freeze Dryer. A 10% solution of a given polymer was first made by dissolving the polymer into nanopure water. After dissolution was complete, a portion of the polymer solution was placed in a small volume vial and placed in a −80° C. freezer. After at least 24 hours, the vial was removed and placed into the freeze dryer. A constant vacuum was applied of at least 0.2 torr. After at least 24 hours the vial was removed from the apparatus. The lyophilized (freeze dried) foam was then removed from the vial as a circular disc.

This has been performed with:
1. 100% Hydrolyzed Poly-Vinyl Acetate (PVAc)
2. 87% Hydrolyzed PVAc

Example 2

Preparation and Characterization of a Typical Ring-Shaped Disc

Foams produced as in example 1 were taken and cut to produce a ring shape disc with an outer and inner diameter of 2 and 1.7 cm respectively and a thickness of 2 mm. The pore fraction of the 100% hydrolyzed Poly-Vinyl Acetate (PVAc) foam was found to be about 0.9. The size of pores shown, via microscopy, was about 1-5 um.

Example 3

General Method of Preparing a Flexible Barrier Film by Compression Molding

Polycaprolactone pellets were placed between 2 steel plates. Theses plates were then placed in a hot press preheated to 80° C. After allowing 10 minutes for equilibration, the polymer was pressed with 4000 lbs for 15 minutes. After slow cooling to room temperature, the film was removed and measured to be approximately 0.15 mm in thickness. This film was then cut to squares slightly larger than the prefabricated foam pieces. The PCL pieces were placed on top of the foam and placed in a 130° C. oven for 30 seconds. The combined foam and film composite was removed and allowed to cool for 10 minutes.

Example 4

Properties of a Typical Composite and the Film Component Thereof

Foam composed of 100% Hydrolyzed PVAc was lyophilized and laminated as seen in Examples 1 and 3. This was then cut into 11 by 6 mm rectangular pieces. A 3-point bending test was conducted using an MTS Synergie 200. The results are summarized in Tables I to IV.

TABLE I

Flexural Properties of Foam/Film Composite

| Run | Thickness (mm) | Width (mm) | Flexural Strength (Kpsi) | Modulus (MPa) | Strain at Peak (%) |
|---|---|---|---|---|---|
| 1 | 1.4 | 6.0 | 1.8 | 40.3 | 4.4 |
| 2 | 1.6 | 5.0 | 2.0 | 48.2 | 6.1 |
| 3 | 1.5 | 5.5 | 1.9 | 44.2 | 4.7 |
| 4 | 1.6 | 5.3 | 2.5 | 86.7 | 4.4 |
| Average | 1.5 | 5.5 | 2.1 | 54.9 | 4.9 |

The 0.2 mm thick Polycaprolactone films were tested separately using the 3-point bending method. These results are seen in Table II.

TABLE II

Flexural Properties of Film Only

| Run | Thickness (mm) | Width (mm) | Flexural Strength (Kpsi) | Modulus (MPa) | Strain at Peak (%) |
|---|---|---|---|---|---|
| 1 | 0.2 | 5.8 | 5.2 | 24.3 | 2.3 |
| 2 | 0.19 | 6.5 | 3.6 | 19.1 | 2.0 |
| 3 | 0.2 | 6.0 | 3.8 | 25.3 | 2.1 |
| Average | 0.2 | 6.1 | 4.2 | 22.9 | 2.1333 |

Tensile testing was also performed using vice-style grips w/0.5" gage length. These results are shown in Table III.

TABLE III

Tensile Properties of Film* Only

| Run | Width (mm) | Thickness (mm) | Tensile Strength (Kpsi) | Modulus (MPa) | Orient Load (N) |
|---|---|---|---|---|---|
| 1 | 0.5 | 0.2 | 59.9 | 160 | 29 |
| 2 | 0.5 | 0.2 | 53.8 | 204 | 34 |
| 3 | 0.5 | 0.2 | 52.8 | 200 | 32 |
| Average | 0.5 | 0.2 | 55.5 | 188 | 31.66 |

*Ultimate elongation exceeded 200%.

To study affect of water simulating the actual eye environment, prewet composites were tested for their flexural properties. Results are seen in Table IV.

TABLE IV

Flexural Properties of Wetted Film/Foam Only

| Run | Thickness (mm) | Width (mm) | Flexural Strength (Kpsi) | Modulus (MPa) | Strain at Peak (%) |
|---|---|---|---|---|---|
| 1 | 1.3 | 6.3 | 0.10 | 0.62 | 10.4 |
| 2 | 1.3 | 6.0 | 0.06 | 0.75 | 6.0 |
| 3 | 1.4 | 6.2 | 0.09 | 0.46 | 11.1 |
| 4 | 1.4 | 5.9 | 0.08 | 0.47 | 9.8 |
| Average | 1.4 | 6.1 | 0.07 | 0.57 | 9.3 |

Example 5

Typical Method for Producing of a Drug Loaded Foam with a Water Soluble Drug A 10% solution of about 87% hydrolyzed poly-vinyl acetate (PVAc) was prepared by dissolving 4 g of PVAc in 40 mL of nanopure water. One-fifth of a gram of dexamethasone disodium phosphate (DSP) was concurrently dissolved in 1 mL of nanopure water. Two grams of the fully dissolved 10% PVAc solution was placed in a vial along with 1 mL of the DSP dissolved in water. This solution was allowed to dissolve for an additional 24 hours at room temperature. The vial was placed in the −80° C. freezer for 24 hours. The solution was then placed into a Labconco freeze dryer for 24 hours. Upon removal, a freeze-dried foam loaded with drug was isolated as a circular disc.

Example 6

Preparation of a Typical Microporous Foam by Freeze Drying

A 10% solution of practically fully hydrolyzed poly-vinyl acetate (PVAc) was made by dissolving 4 grams of 100% hydrolyzed PVAc in 40 mL of nanopure water. The polymer was allowed to dissolve for 24 hours. Two grams of our solution was weighed and transferred to a vial. The vial was placed in the −80° C. freezer for 24 hours. The solution was then placed into a Labconco freeze dryer for 24 hours. Upon removal, a freeze-dried foam was produced as a circular disc.

Example 7

Assembly of a Typical Foam-Film Composite and Cutting of a Crescent-Shaped Disc: A General Method Polycaprolactone pellets were placed between 2 steel plates. Theses plates were then placed in a hot press preheated to 80° C. After allowing 10 minutes for equilibration, the polymer was pressed with 4000 lbs for 15 minutes. After slow cooling to room temperature, the film was removed and measured to be approximately 0.15 mm in thickness. This piece was then placed on top of a foam of practically the same area and placed in a 130° C. oven for 30 seconds. The adjoined foam/film composite pieces were removed and allowed to cool for 10 minutes. The composite sheet was then cut using a $15/16$ inch punch. This circle was punched 7 mm from the base of the outer circle with a $9/16$ inch. Curved clippers were used to round the sharp edges of the narrow free side arms of the device. Thus a composite crescent-shaped delivery device was designed to fit onto the sclera as shown in FIGS. 1 to 3. FIGS. 4 to 6 depict the basic crescent-shaped device with two side flaps for better fit on the sclera. The flaps were cut using a proper set of punches.

Figure 7:
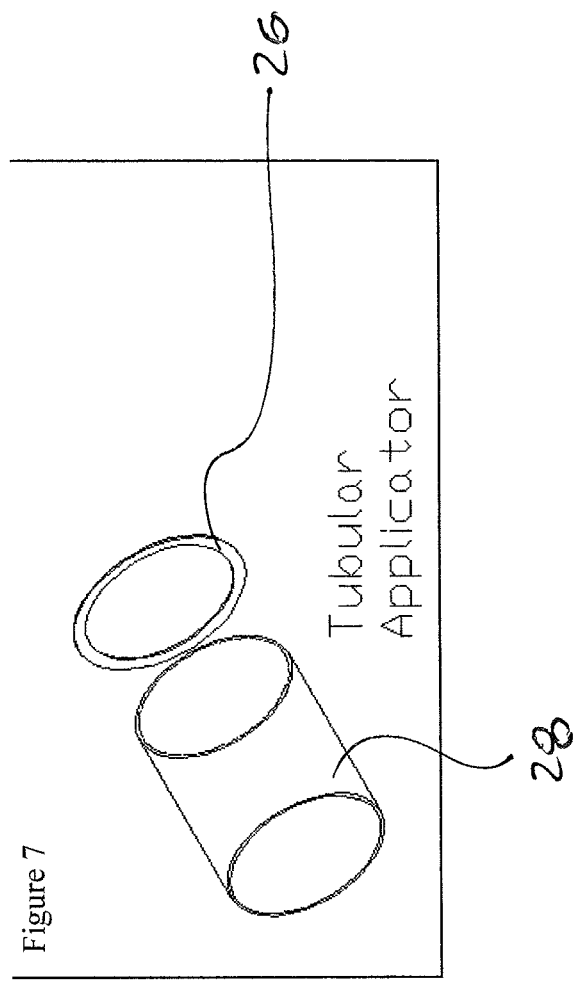
FIG. 7 is a perspective view of a disc and tubular applicator in accordance with another embodiment of the present invention.

Alternatively, the crescent-shaped device is replaced by a flat, ring-shaped circular composite disc that is affixed securely to the bottom perimeter of a tubular applicator as depicted in FIG. 7. A method of assembling the disc/applicator system is outlined in Example 8. If the cross-section of the tubular applicator is elliptical in shape, an elliptical ring can be produced in a similar manner.

Example 8

Assembly of a Typical Foam-Film Composite and Cutting into Ring-Shaped Disc: A General Method Polycaprolactone pellets were placed between 2 steel plates. Theses plates were then placed in a hot press preheated to 80° C. After allowing 10 minutes for equilibration, the polymer was pressed with 4000 lbs for 15 minutes. After slow cooling to room temperature, the film was removed and measured to be approximately 0.15 mm thick. This piece was then placed on top of a foam having a comparable perimeter and placed in a 130° C. oven for 30 seconds. The combined pieces were removed and allowed to cool for 10 minutes. The composite sheet was then cut using a $13/16$ inch punch. Another circle was punched in the middle of the outer circle with a $7/16$ inch punch. Thus a composite circular shaped delivery device was ready for use.

Example 9

A Typical Method for Loading the Drug Solution and Evaluating the Drug Delivery Profile A foam-film composite made using the process outlined in example 3 was used to evaluate the drug delivery profile of said composite after drug loading. This was done by loading a dry 1×1 cm piece of the composite foam-film with 100 μL of our 261.5 mg/mL solution of dexamethasone disodium phosphate in nanopure water. This piece was then placed on top of a wetted 2×2 cm piece without the flexible film. These two pieces were left in contact for a period of 10 minutes at 37° C. After two minutes the pieces were separated and the receptor (bottom) piece was placed into a vial. At this point 5 mL of water was added to the vial and the piece was shaken in this new volume of water for 10 minutes. The aqueous layer was then filtered through a 0.45 μm filter and run on a reverse phase HPLC. Using a C18 column and a 12 minute gradient method of water and acetonitrile, it was determined that about 12 mg or about 45% of the loaded DSP diffused to the receptor (bottom) piece.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicant hereby discloses all subranges of all ranges disclosed herein. These subranges are also useful in carrying out the present invention.

What is claimed is:

1. A partially microcellular, selectively hydrophilic composite for ocular delivery of at least one bioactive agent, the composite comprising:
   a hydrophilic microcellular foam capable of being loaded with at least one bioactive agent and adjoined with a flexible hydrophobic barrier polymeric film;
   wherein a contact side of the foam is configured to engage a surface and an opposing side of the foam is configured to be oriented away from the surface;
   wherein the flexible hydrophobic barrier polymeric film has a comparable perimeter approximately equal to a comparable perimeter of the hydrophilic microcellular foam and the polymeric film covers the opposing side of the foam oriented away from the surface and is attached to at least a portion of the opposing side of the hydrophilic microcellular foam;
   wherein the polymeric film and microcellular foam form a stacked construct with exposed, non-overlapped sides with the polymeric film forming the outermost layer from the surface and the foam forming the innermost layer; and
   wherein the at least one bioactive agent is dispersed throughout cells of the hydrophilic microcellular foam.

2. A partially microcellular, selectively hydrophilic composite as in claim 1 wherein the hydrophilic microcellular foam comprises an open cell structure of at least one freeze-dried polymer selected from the group consisting of polyvinyl alcohol, poly(vinyl alcohol-co-vinyl acetate), an hydroxyalkyl cellulose, polyethylene oxide, polyvinyl pyrrolidone, poly(vinyl acetate-co-vinyl pyrrolidone), a polyether-ester, a polyether-ester-urethane, poly(methyl methacrylate-co-vinyl pyrrolidone), poly(ethylene-co-vinyl alcohol), and poly(hydroxy-ethyl methacrylate-co-alkyl methacrylate).

3. A partially microcellular, selectively hydrophilic composite as in claim 1 wherein the flexible hydrophobic barrier polymeric film comprises at least one polymer selected from the group consisting of polydimethylsiloxane, poly-ε-caprolactone, polyethylene adipate, polytetramethylene adipate, low density polyethylene, poly(ethylene-vinyl acetate), and a polyalkylene succinate.

4. A partially microcellular, selectively hydrophilic composite as in claim 2 wherein the freeze-dried foam has a thickness of from about 1 to about 3 mm, a pore fraction of at least 0.5 to 0.9 and an average pore diameter of from about 1 to about 400 microns.

5. A partially microcellular, selectively hydrophilic composite as in claim 4 wherein the at least one bioactive agent is soluble or dispersed solid nanoparticles or microparticles of at least one bioactive agent selected from the group consisting of steroidal anti-inflammatory drugs, non-steroidal anti-inflammatory drugs, vasoconstricting drugs, antimicrobial agents, antiviral agents, antiretroviral agents, antineoplastic agents, and drugs used for treating glaucoma and other eye disorders.

6. A partially microcellular, selectively hydrophilic composite as in claim 3 wherein the flexible hydrophobic barrier film is made by compression molding or solution casting and adjoined with the microcellular foam by thermoforming at 50 to 150° C., solvent or ultrasonic welding or crosslinkable prepolymeric intermediates.

7. A partially microcellular, selectively hydrophilic composite as in claim 6 wherein the flexible hydrophobic barrier film itself exhibits a flexural modulus of less than 30 MPa, a tensile strength of more than 50 Kpsi, an ultimate elongation of at least 200%, and melts or softens below 150°, the assembled composite construct, presoaked for less than 10 minutes with water using about 100 μL per 120 mm$^3$, displaying a flexural modulus of less than 1 MPa.

8. A partially microcellular, selectively hydrophilic composite as in claim 5 wherein the steroidal anti-inflammatory drug comprises a dexamethasone disodium phosphate, the vasoconstricting drug comprises oxymetazoline, and the antimicrobial drug comprises triclosan or triclosan sodium.

9. A partially microcellular, selectively hydrophilic composite as in claim 4 wherein the at least one bioactive agent is an aqueous solution of at least one bioactive agent selected from the group consisting of steroidal and non-steroidal drugs, vasoconstricting drugs, antimicrobial drugs, antineoplastic drugs, antiviral and antiretroviral agents, and drugs used for treating glaucoma and other eye disorders.

10. A partially microcellular, selectively hydrophilic composite as in claim 9 wherein the steroidal agent comprises dexamethasone disodium phosphate, the vasoconstricting drug comprises oxymetazoline and the antimicrobial drug is selected from triclosan and triclosan sodium.

11. A partially microcellular, selectively hydrophilic composite as in claim 1, wherein the composite comprises a crescent-shaped ocular drug delivery device with rounded free ends.

12. A partially microcellular, selectively hydrophilic composite as in claim 11 wherein the crescent-shaped device is designed for initial deployment at the rim of the conjunctiva for subsequent upward movement to partially cover the sclera forming a film without interfacing with the cornea through vertical or horizontal movement.

13. A partially microcellular, selectively hydrophilic composite as in claim 12 with two lateral flaps extending across the surface to further stabilize the position of the device at the application site.

14. A partially microcellular, selectively hydrophilic composite as in claim 1 in the form of a ring-shaped disc affixed to an applicator wherein the disc is designed to define an interior opening and have a lumen diameter with a difference between an outside and an inside diameter of at least 3 mm wherein the disc is configured to cover a portion of the surface.

15. A partially microcellular, selectively hydrophilic composite as in claim 4 suitable for loading with a solution of the bioactive agent(s) in less than 10 minutes and delivering of at least 30% of the bioactive agent(s) at the ocular site in less than 10 minutes.

16. A partially microcellular, selectively hydrophilic composite as in claim 1 as a component of an iontophoretic ocular delivery device configured for delivery of at least one bioactive agent to the surface wherein features adjacent the surface form a counter pole and wherein a flexible conductive film or mesh is sandwiched securely between the hydrophilic microcellular foam and the hydrophobic barrier film and the conductive film or mesh is further connected to one pole of a direct current mini-battery to function as an iontophoretic system to allow the iontophoretic transport of the bioactive agent from the microcellular foam to the surface.

17. A partially microcellular, selectively hydrophilic composite as in claim 16 wherein the flexible film or mesh of the iontophoretic delivery system is made of a conductive metal or surface- or bulk-conducting polymer having a maximum thickness of less than 500 micron.

18. A partially microcellular, selectively hydrophilic composite as in claim 17 wherein the metal film or mesh comprises at least one metal selected from the group consisting of silver, gold, platinum, titanium, copper, iron alloys, or chrome alloys, the surface conducting polymer comprises a sulfonated polyalkylene with doped covalently bonded polypyrrole and the bulk-conducting polymer comprises carbon fibers.

19. A partially microcellular, selectively hydrophilic composite as in claim 1 capable of being loaded with a solution of the bioactive agent(s) in less than 10 minutes and delivering of at least 30% of the bioactive agent(s) at the ocular site in less than 10 minutes.

20. A partially microcellular, selectively hydrophilic composite as in claim 2 capable of being loaded with a solution of the bioactive agent(s) in less than 10 minutes and delivering of at least 30% of the bioactive agent(s) at the ocular site in less than 10 minutes.

* * * * *